(12) United States Patent
Breil et al.

(10) Patent No.: US 8,552,369 B2
(45) Date of Patent: Oct. 8, 2013

(54) OBTAINING ELEMENTAL CONCENTRATION PROFILE OF SAMPLE

(75) Inventors: Nicolas Breil, Hopewell Junction, NY (US); Jerome Bienacel, Reaumont (FR)

(73) Assignees: International Business Machines Corporation, Armonk, NY (US); STMicroelectronics (Crolles 2) SAS, Crolles (FR)

( * ) Notice: Subject to any disclaimer, the term of this patent is extended or adjusted under 35 U.S.C. 154(b) by 0 days.

(21) Appl. No.: 13/366,749

(22) Filed: Feb. 6, 2012

(65) Prior Publication Data

US 2012/0280124 A1 Nov. 8, 2012

(30) Foreign Application Priority Data

May 3, 2011 (EP) .................................... 11305521

(51) Int. Cl.
*H01J 40/00* (2006.01)
(52) U.S. Cl.
USPC .......................................................... 250/305
(58) Field of Classification Search
USPC .......................................................... 250/305
See application file for complete search history.

(56) References Cited

U.S. PATENT DOCUMENTS

| | | | | |
|---|---|---|---|---|
| 5,068,535 A | * | 11/1991 | Rabalais | 850/16 |
| 5,635,714 A | * | 6/1997 | Nablo et al. | 250/305 |
| 6,255,003 B1 | * | 7/2001 | Woodard et al. | 428/623 |
| 6,800,852 B2 | * | 10/2004 | Larson et al. | 250/305 |
| 7,456,399 B1 | * | 11/2008 | Soderstrom | 250/305 |
| 8,269,167 B2 | * | 9/2012 | deCecco et al. | 250/305 |
| 2004/0135081 A1 | * | 7/2004 | Larson et al. | 250/305 |
| 2004/0157122 A1 | * | 8/2004 | Naoi et al. | 429/213 |
| 2008/0042057 A1 | * | 2/2008 | Sanada et al. | 250/305 |
| 2008/0283743 A1 | * | 11/2008 | deCecco et al. | 250/305 |
| 2009/0291371 A1 | * | 11/2009 | Konishiike et al. | 429/338 |
| 2012/0168623 A1 | * | 7/2012 | Edelmann et al. | 250/305 |

OTHER PUBLICATIONS

S. Wolf, R.N. Tauber, "Silicon Processing for the VLSI Era", Lattice Press: Sunset Beach, CA, 1986, vol. 1, Process Technology, p. 607.
T. Hori, "Gate Dielectrics and MOS ULSIs", Springer Series in Electronics and Photonics, vol. 34, Springer-Verlag, Berlin, 1997, p. 274-276.

* cited by examiner

*Primary Examiner* — Robert Kim
*Assistant Examiner* — Jason McCormack
(74) *Attorney, Agent, or Firm* — Yuanmin Cai (57) ABSTRACT

A method of obtaining an elemental concentration profile of a sample using x-ray photon spectroscopy measurements is described. Each measurement relates to a different depth in the sample. The sample is shaped to provide access to different depths thereof. Measurements are obtained at respective positions on a bevelled surface exposing material at each of the depths. The method involves fitting the measurements to a mathematical function, dividing the function into a plurality of equal depth wise slices, determining the elemental concentration for the slice corresponding to the thinnest part of the bevel, and then iteratively determining the contribution of each successive slice to the intensity value as being the intensity value measured for that slice minus the intensity value determined to have been contributed by each preceding slice. According to preferred embodiments, a surface correction factor compensating surface effect phenomena is applied to the concentration value calculated for each slice.

7 Claims, 7 Drawing Sheets

OBTAINING ELEMENTAL CONCENTRATION PROFILE OF SAMPLE

CROSS REFERENCE TO RELATED APPLICATION

The present application claims the benefit of priority of European Patent Application Serial Number EP11305521.4 filed May 3, 2011 with the European Patent Office, the content of which is incorporated herein by reference in its entirety.

FIELD OF THE INVENTION

The present invention relates to a method of obtaining an elemental concentration profile of a sample, and in particular of obtaining a concentration profile for Nitrogen in a semiconductor sample.

BACKGROUND

For technological development, the determination of an element profile in a material (e.g. Nitrogen profile in a SiO2 layer, in High-K) is of major importance.

A number of techniques are known which may be helpful in obtaining such a profile.

Secondary Ion Mass Spectroscopy (SIMS) gives some insight into nitrogen concentration distribution. This approach has the disadvantage however of being suitable only for off-line use, and is furthermore time-consuming preventing fast and extensive investigation. Still further, the SIMS technique is subject to measurement uncertainties due to the surface of the Cesium analysis beam, the induced crater during sputtering, and matrix effects, as described for example in S. Wolf, R. N. Tauber, "*Silicon Processing for the VLSI Era*", Lattice Press: Sunset Beach, Calif., 1986, Volume 1, Process Technology, p. 607.

Nuclear characterization techniques, such as Nuclear Reaction Analysis (NRA) and Medium Energy Ion Scattering (MEIS), give some meaningful information on the material properties, such as absolute quantification of the elements for NRA, element ratios through the film, and multi-layer interdiffusion for MEIS. However, these techniques are not available inline. Facilities are costly and scarce, and usually require a lot of time to perform and analyze.

Auger depth profiling is similarly time-consuming and solely available off-line.

Generally, these solutions are time consuming, require an expert skilled in the art of performing these analysis, are costly, and time-consuming.

Also, these techniques are destructive and always performed off-line (out of the cleanroom).

Some in-line tools can give some information on the nitrogen profile. For example, the X-ray Photoelectron Spectroscopy (XPS) in-line tool allows measurements of SiON films, and provides access to the nitrogen dose and to its chemical bonding at the surface.

Primarily used as a fullsheet surface measurement technique, X-ray Photoelectron Spectroscopy (XPS) applications can be extended to element profile investigation using specific sample preparations that induce a bevel via wet etching of the films. The most advanced developments of this technique, initiated by J. Bienacel, in the article entitled "Développement d'un procédé de nitruration plasma des oxydes de grille pour le noeud technologique 65 nm>>, PhD thesis, Université de Marseille, 2005. This XPS measurement gives an integrated dose for a given and already known element distribution in the film, which has to be calibrated beforehand. This technique is routinely used for nitrogen dose measurement of thin gate oxynitride (65/45 nm CMOS thin gate oxides with thicknesses of 15 to 30 Å for example). However, one has to note that the photoelectron escape length is in the order of 40-50 Å, which prevents the use of this tool for interface nitridation in 100 Å thick films (e.g. tunnel oxide). Some XPS tools include an argon sputtering feature that can provide access to the depth of the material. However, such tools are subject to the same kind of measurement errors as all sputtering techniques, such as SIMS.

Thus although the nitrogen characteristics in gate oxide dielectrics are of paramount importance for device operation and reliability as described in the relevant pages of the book by T. Hori, entitled "*Gate Dielectrics and MOS ULSIs*", Springer Series in Electronics and Photonics, vol. 34, Springer-Verlag, Berlin, 1997, none of the available cleanroom inline techniques can provide access to this information.

It is accordingly desirable to develop a fast, accurate, and in-line characterization technique for use in particular in the characterization of the nitrogen profile in gate oxynitride films.

SUMMARY

According to the present invention there is provided a method of obtaining an elemental concentration profile of a sample according to the appended independent claim 1, an apparatus according to the appended claim 7, a computer program according to the appended claim 8 and a computer readable medium according to the appended claim 9. Preferred embodiments are defined in the appended dependent claims.

The present invention offers the advantage of compatibility with patterning methods available in cleanroom. The present invention offers the further advantage that a full range of material thickness can be analyzed. The method in accordance with the present invention permits an element profile determination. The technique is fast, cost effective, can be used inline, and brings information related to the electronic binding configuration of the element that only the XPS technique can give.

Embodiments of the present invention offer a fast, repeatable and inline nitrogen profile measurement.

Further advantages of the present invention will become clear to the skilled person upon examination of the drawings and detailed description. It is intended that any additional advantages be incorporated herein.

BRIEF DESCRIPTION OF THE DRAWINGS

Embodiments of the present invention will now be described by way of example with reference to the accompanying drawings in which like references denote similar elements, and in which.

DETAILED DESCRIPTION

In accordance with embodiments of the present invention, it is proposed to suggest to use a patterning method available in the cleanroom (dry etch, wet etch, CMP etc.), that can produce a <<bevel>> profile on the material sample to be analyzed. Then, a series of XPS measurements can be performed along a wafer diameter, so that a full range of material thickness can be analyzed. Using the adapted data extraction, and treatment, the XPS information can lead to the element profile determination.

Figure 1:
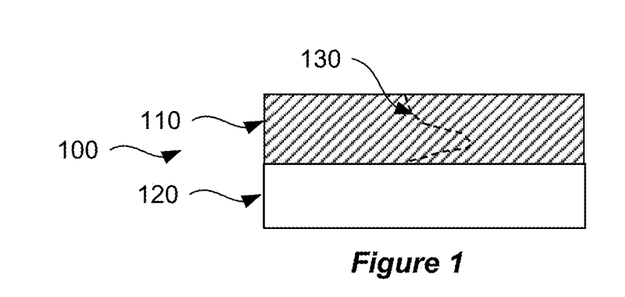
FIG. 1 shows a cross-sectional view of a nitrided SiON layer before the beveled profile formation.

FIG. 1 shows a cross-sectional view of a nitrided SiON layer before the beveled profile formation.

As shown in FIG. 1, there is provided a wafer 100 comprising a nitrided silicon oxide layer 110 grown on a silicon substrate 120. The nitrided silicon oxide layer 110 is characterised by a nitrogen profile, which is schematically represented in cross-section view by the curve 130.

Starting from the wafer of FIG. 1, a bevel may be formed at the edges thereof. For example, the sample preparation consists in using an asymmetric wet etching in a single wafer equipment such as for instance Applied Material Oasis, Dainippon Screen SU-3000/3100. A "bevel" pattern can be obtained using a fluoridic acid dispensed along the wafer radius. The centrifugal force happening on the dispensed chemistry during a wafer rotation will induce a more pronounced etching of the outer part of the radius. The bevel shape can be adjusted depending on the material composition and concentration, by changing the wafer rotation speed, the dispense pattern, and the chemistry concentration and temperature. Other techniques may be used to produce the bevel as will be apparent to the skilled person, using for example dry etch, wet etch, CMP techniques etc.

Figure 2:
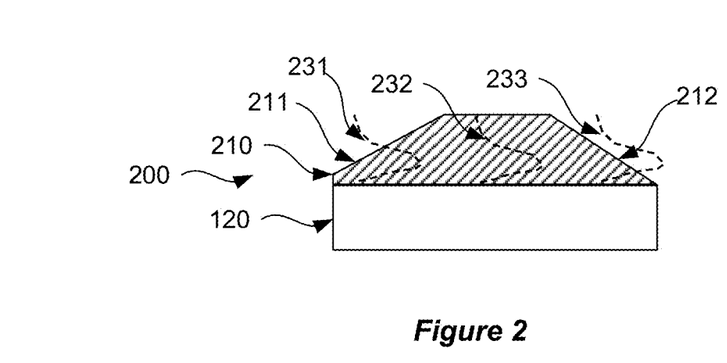
FIG. 2 shows a cross-sectional view of a nitrided SiON layer after the beveled profile formation.

FIG. 2 shows a cross-sectional view of a nitrided SiON layer after the beveled profile formation.

As shown in FIG. 2, the wafer 200 comprises a nitrided silicon oxide layer 210 grown on a silicon substrate 120. The nitrided silicon oxide layer 210 has been etched to form bevelled areas 211 and 212. These bevelled areas thus expose complete cross sections of the nitrided silicon oxide layer 210 such that different parts of the nitrogen profile 130 are exposed along the radius of the wafer to measurement from above, that is, parallel to the axis of the wafer.

In particular, once the bevelled profiles are formed, an X-ray Photoelectron Spectroscopy (XPS) measurement may be performed.

An exemplary procedure to determine the oxynitride thickness at a given measurement point using the Si2p XPS spectra will now be discussed.

First of all, the Si2p XPS spectrum is measured, and the background noise is removed using a linear subtraction algorithm.

A method based on the calculation of the ratio of $A_{Si-O}$ over $A_{Si-Si}$, respectively the Si—O bond area and the Si—Si bond area for different nitrided silicon oxide layer thicknesses.

Figure 3:
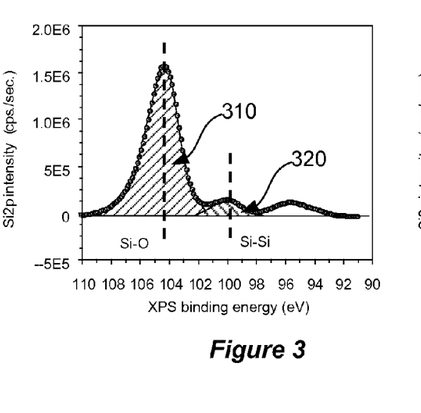
FIG. 3 shows a first Si2p XPS spectrum of a SiON oxynitride. More particularly, the spectrum of FIG. 3 corresponds to a silicon oxide layer thickness of 60 Angstrom.

FIG. 3 shows a first Si2p XPS spectrum of a SiON oxynitride. More particularly, the spectrum of FIG. 3 corresponds to a silicon oxide layer thickness of 60 Angstrom.

By way of example, the XPS spot size may be set to 4×10 mm, and the XPS take-off angle set to 10°.

As shown in FIG. 3, the Si2p XPS spectrum of a SiON oxynitride exhibits an Si—O bond area 310 and an Si—Si bond area 320. From these regions are derived values for $A_{Si-O}$ and $A_{Si-Si}$, the ration between which is then used to calculate the oxide thickness $t_{SiO2}$ using the following relation:

$$t_{SiO2} = \lambda \cdot \sin(\theta) \cdot \ln\left[(K \cdot A_{Si-O}/A_{Si-Si}) + 1 - L_{cor}\right] \qquad \text{eq. I}$$

with $\lambda$ the mean free path of the emitted photoelectrons, $\theta$ the detector angle with the sample normal, K a calibration factor depending on the incident photon flux, on the incident X-ray beam surface, and on the photo ionization characteristics of the analyzed element in the considered material, and $L_{cor}$ an additional correction term.

Further details of this technique may be found in U.S. Pat. No. 6,800,852 to P. E. Larson, D. G. Watson, J. F. Moulder, "Nondestructive characterization of thin films using measured basis spectra", Revera Corporation. The precision of this method has been verified by comparison with ellipsometry measurements. Excellent correlation has been found to exist between the two methods.

Figure 4:
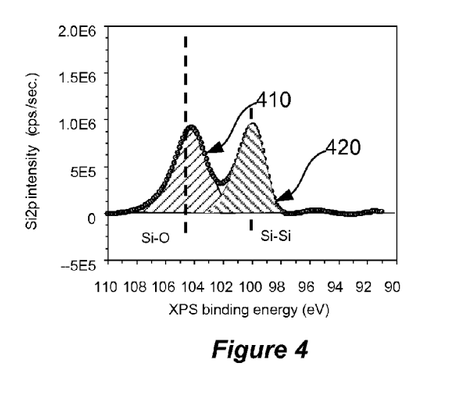
FIG. 4 shows a second Si2p XPS spectrum of a SiON oxynitride.

FIG. 4 shows a second Si2p XPS spectrum of a SiON oxynitride. More particularly, the spectrum of FIG. 4 corresponds to a silicon oxide layer thickness of 30 Angstrom.

As shown in FIG. 4, the Si2p XPS spectrum of a SiON oxynitride exhibits an Si—O bond area 410 and an Si—Si bond area 420 similarly to FIG. 3.

From a qualitative point of view, it can be seen that the Si—O bond area 310, 410 decreases along with the oxide thickness, because the quantity of Si—O bonds decreases with the material thickness. On the other hand, the Si—Si bond area 320, 420 coming from the Si substrate 120 increases due to the reduced shielding effect of the thinner sample.

While only two different silicon oxide layer thicknesses have been discussed with reference to FIGS. 3 and 4, it will be appreciated that any arbitrary number of readings may be taken, for a corresponding number of different sample thicknesses. By increasing the number of reading sets, the different Si2p XPS spectra can be computed to obtain the thickness profile along the wafer diameter.

Figure 5:
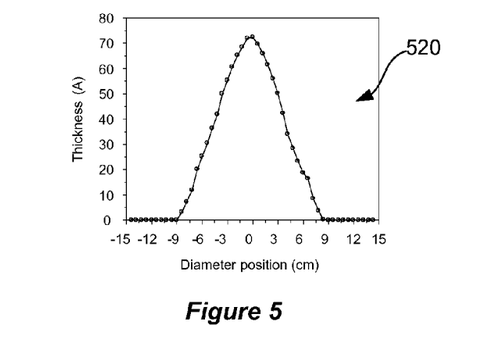
FIG. 5 shows a thickness profile calculated using the Si2p XPS spectra along the diameter of a SiON wafer after a beveled wet etching.

FIG. 5 shows a thickness profile calculated using the Si2p XPS spectra along the diameter of a SiON wafer after a beveled wet etching. More particularly, FIG. 5 shows the results of performing the measurements of FIGS. 3 and 4 for 49 different radial values. As shown, measurements falling to either side of the wafer 200 produce 0 thickness values, whilst readings falling within the diameter of the wafer 200 tend to a maximum over 70 Angstrom towards the center of the wafer, whilst approaching 0 at the edges. The symmetry of the profile confirms that the bevel wet etch process is radial.

Now that precise thickness values are available for a set of radial positions, XPS measurements can be performed for these positions.

Figure 6:
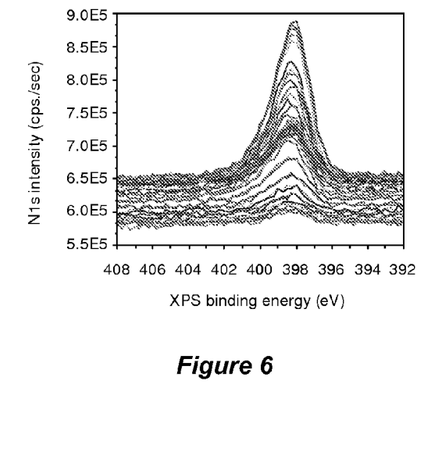
FIG. 6 shows XPS N1s raw spectra of the 49 measurement points along the wafer diameter, each spectra corresponding to a thickness point shown in FIG. 5.

FIG. 6 shows XPS N1s raw spectra of the 49 measurement points along the wafer diameter, each spectra corresponding to a thickness point shown in FIG. 5.

As shown in FIG. 6, each of the 49 measurements produces a separate curve plotting intensity from $5.5 \times 10^5$ to $9 \times 10^5$ counts per second per second across a range of binding energies from 392 to 408 eV.

These N1s XPS spectra are measured and computed using the same background removal algorithm.

Figure 7:
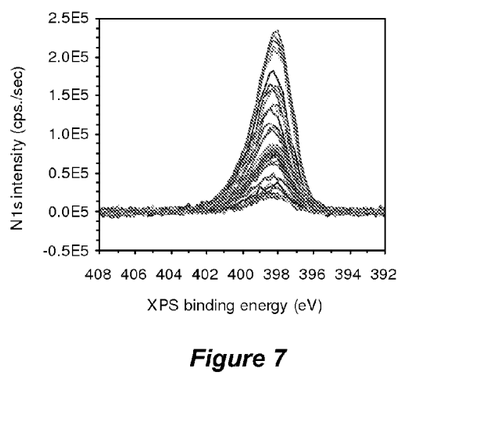
FIG. 7 shows XPS N1s background-subtracted spectra of the 49 measurement points along the wafer diameter, each spectrum corresponding to a thickness point shown in FIG. 5.

FIG. 7 shows XPS N1s background-subtracted spectra of the 49 measurement points along the wafer diameter, each spectrum corresponding to a thickness point shown in FIG. 5.

Important variations of these N1s spectra as a function of the measurement point are visible, which must be related to the changes in the nitrogen detection as a function of the oxide thickness remaining.

Since that the XPS spectra area of a given element is proportional to the elemental quantity of the element in the analyzed material, a first approximation of the nitrogen profile may be obtained by plotting the integral of the background-subtracted spectrum as shown in FIG. 7 for each respective thickness value, against thickness.

Figure 8:
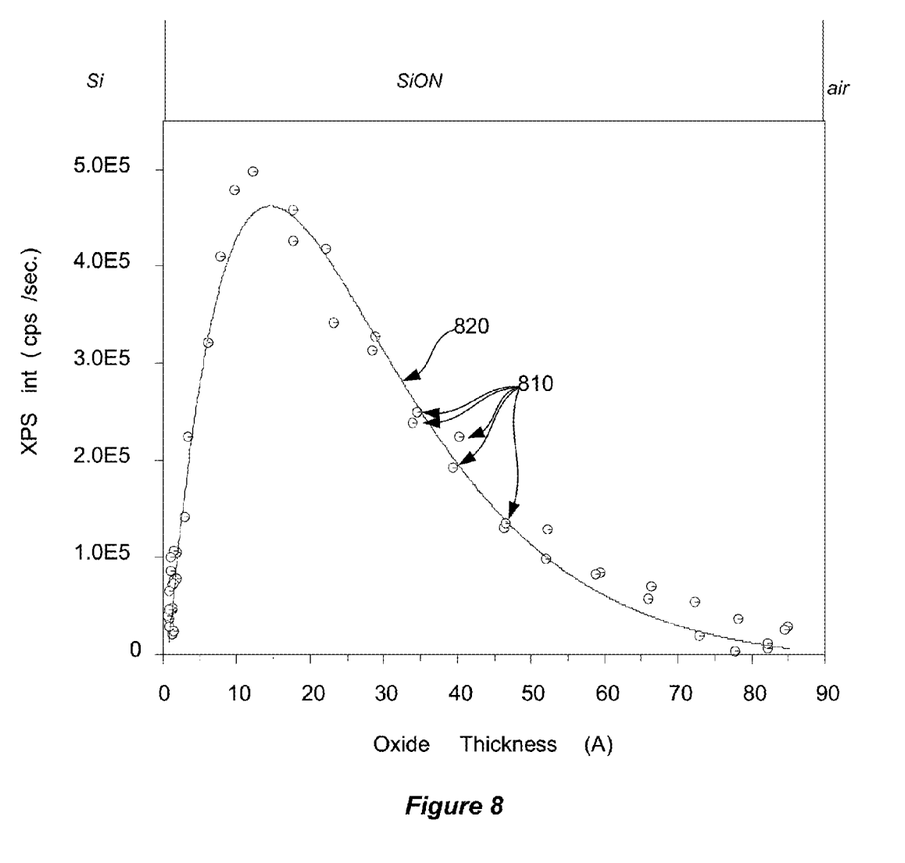
FIG. 8 shows a plot of integral of the background-subtracted spectrum as shown in FIG. 7 for each respective thickness value, against thickness.

FIG. 8 shows a plot of integral of the background-subtracted spectrum as shown in FIG. 7 for each respective thickness value, against thickness.

More particularly, as shown in FIG. 8 the raw data 810 for each thickness calculation are shown as open circles, and a curve 820 based on a sum of exponential functions is fitted to these data. It will be appreciated that any suitable mathematical function, e.g. a gamma function etc. may be selected as appropriate.

A "Generic Attenuation Function" can be defined, whereby $G=f(x,\lambda,\theta)$, with x, $\lambda$, $\theta$ keeping the same signification as above.

Thus, the expression of the XPS signal intensity IN1s measured corresponding the nitrogen located at a given depth, can be given by:

$$I_{N1s} = K \int_0^{t_{ox}} C_{N1s}(x) \cdot G(x, \lambda, \theta) \cdot dx$$

Of course, changing this first equation would imply changing the derivation forming the base of the algorithm, including the correction factor discussed further hereafter.

The XPS signal attenuation going through a certain thickness of a given material, is widely considered to obey an exponential decrease. Accordingly it is proposed to adopt an exponential function for the modelling of the response. Nevertheless, the exponential decay is merely a convenient form of describing this decay, but not necessarily the exact physical description of what is happening, so that other bases may be envisaged.

The raw profile 810 is fitted using a sum of exponential functions, whereby the general relationship between $I_{N1s}$ and the element concentration $C_{N1s}$ is given by:

$$I_{N1s} = K \int_0^{t_{ox}} C_{N1s}(x) \cdot \exp\left(\frac{-x}{\lambda \cdot \cos\theta}\right) \cdot dx, \qquad \text{eq. II}$$

with K a calibration factor mentioned above, x the depth from the surface of the material, $\lambda$ the mean free path of the emitted photoelectrons in the material, and $\theta$ the angle between the analyzer and the direction perpendicular to the sample surface.

This general equation gives an expression of the XPS intensity as a function of the overall nitrogen content in the oxide. However, an objective is to obtain the nitrogen distribution.

Thus, in accordance with embodiments of the present invention there is provided an algorithm based on this first general equation that takes advantage of the XPS-Bevel technique to determine the nitrogen profile.

Starting from the fitted function shown in FIG. 8, the first step consists of separating this intensity profile in slices of an equal thickness $\Delta$.

For example, each slice may be 1 Å thick. The slices are numbered, with the first slices being the closest to the interface with the substrate, and the last slice being at the top surface of the oxide. In the following equations, the index i concerns the slice where the concentration is calculated, and the index j designates the underlying slices that will contribute to the XPS signal according to eq. II. Thus, for a given slice of index i, one will have to calculate the contribution of the underlying slices ranging from j=1 to j=i−1.

Figure 9A:
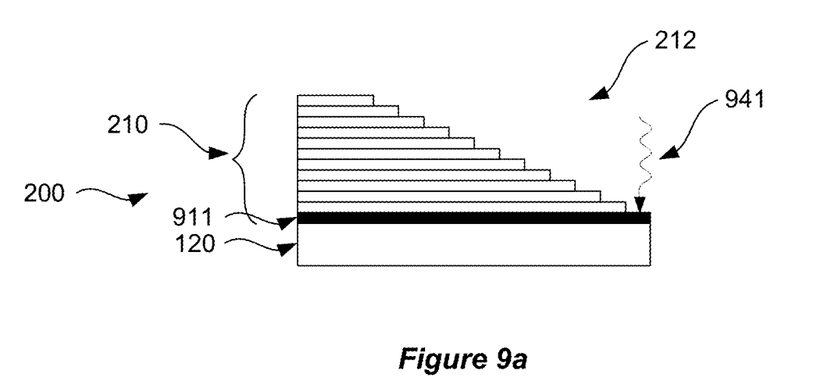
FIG. 9a shows a schematic of the slice method used for determining the nitrogen profile.

FIG. 9a shows a schematic of the slice method used for determining the nitrogen profile. As shown, FIG. 9a shows the bevelled end 212 of the nitrided silicon oxide layer 210 broken schematically into 12 horizontal slices 911 to 922. The first slice analysed 911 is that adjacent the substrate 120, and therefore has no background intensity.

From a partial integration of eq. II, one can express the general intensity contribution from an underlying slice j on the XPS intensity measured on the slice i:

$$I_{N1s}(i, j) = K \cdot A \cdot C_{N1s}(j) \cdot \exp\left[\frac{-(i-j) \cdot \Delta}{A}\right] \cdot \left[1 - \exp\left(\frac{-\Delta}{A}\right)\right] \qquad \text{eq. III}$$

The algorithm starts by applying this general equation to the calculation of the concentration in the first slice (FIG. 9a). Because there is no underlying slice, its contribution in the intensity doesn't exist, and we can use eq. III with i=j=1:

$$I_{N1s}(1, 1) = K \cdot A \cdot C_{N1s}(1) \cdot \left[1 - \exp\left(\frac{-\Delta}{A}\right)\right], \qquad \text{eq. IV}$$

which directly leads to the nitrogen concentration:

$$C_{N1s}(1) = \frac{I_{N1s}(1, 1)}{K \cdot A \cdot \left[1 - \exp\left(\frac{-\Delta}{A}\right)\right]}. \qquad \text{eq. V}$$

The concentration of nitrogen in the first slice $C_{N1s}(1)$ is now known. The eq. III will easily give $I_{N1s}(2,1)$, which is the contribution of this first slice on the XPS intensity measured at the slice i=2. The concentration of the second slice is thus given by:

$$C_{N1s}(2) = \frac{1}{K \cdot A \cdot \left[1 - \exp\left(\frac{-\Delta}{A}\right)\right]} \cdot [I_{N1s}(2, 2) - I_{N1s}(2, 1)] \quad \text{eq. VI}$$

Figure 9B:
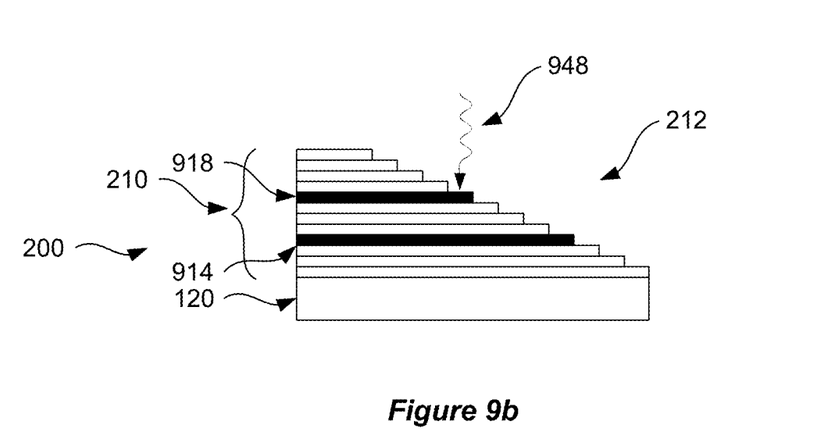
FIG. 9b shows a schematic of the slice method used for determining the nitrogen profile.

FIG. 9b shows a schematic of the slice method used for determining the nitrogen profile. More particularly FIG. 9b shows the slice 914 under consideration, taking into account the contribution to the XPS intensity of the underlying slice 914.

Surface slice, and the nitrogen concentration of a given slice i can be expressed:

$$C_{N1s}(i) = \frac{1}{K \cdot A \cdot \left[1 - \exp\left(\frac{-\Delta}{A}\right)\right]} \cdot \left[I_{N1s}(i, i) - \sum_{j=1}^{j=i-1} I_{N1s}(i, j)\right] \quad \text{eq. VII}$$

Figure 10A:
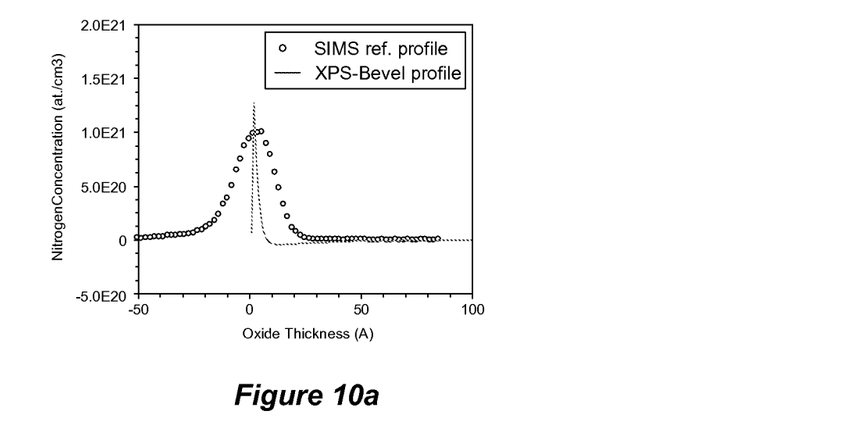
FIG. 10a shows an exemplary XPS-Bevel nitrogen profile obtained in accordance with the foregoing principles in comparison with a SIMS reference profile following a raw algorithm.

One can then generalize this algorithm, and perform iteration from the interface slice to the FIG. 10a shows an exemplary XPS-Bevel nitrogen profile obtained in accordance with the foregoing principles in comparison with a SIMS reference profile following a raw algorithm.

Following the formalism given in the general equations III and VII, FIG. 10a shows a first calibration on a SIMS reference profile of a 95 A thick silicon oxidation that has received a rapid thermal nitridation under NO at 1040° C. during 30 sec. The best fit obtained is shown, from which can be seen that the agreement between the two profiles is not optimal.

In accordance with a preferred embodiment a surface correction factor $\alpha_s$ is introduced in order to take into account the effects that can impact the nitrogen quantification of the surface layer. Considering a given slice i under analysis, when this slice is "buried" in the material at a given thickness, the intensity it delivers at the surface is given by eq. III. Considering the same slice located at the surface of the material due to the etching, the same amount of nitrogen is present in the slice, but the vicinity of the surface can strongly impact this 1 A thick slice. First of all, the surface atoms will show a dangling bond density much higher than in the volume. The XPS analysis being very sensitive to the bonding configuration, this first effect—even If not quantified here—can be of importance in the XPS intensity generated. Then, during the processing of the wet etch bevel, and during the subsequent steps occurring before the analysis, such as contact with atmosphere moisture or the ultra-high vacuum conditions for the XPS analysis, or other atmospheric factors which may lead to modification of the nitrogen concentration of the exposed surface. The surface correction factor $\alpha_s$ takes into account in a phenomenological constant due to the cumulated contribution of these surface effects, and is introduced in eq. VIIb:

$$C_{N1s}(i) = \frac{1}{\alpha_s \cdot K \cdot A \cdot \left[1 - \exp\left(\frac{-\Delta}{A}\right)\right]} \cdot \left[I_{N1s}(i, i) - \sum_{j=1}^{j=i-1} I_{N1s}(i, j)\right] \quad \text{eq. VIIb}$$

Figure 10B:
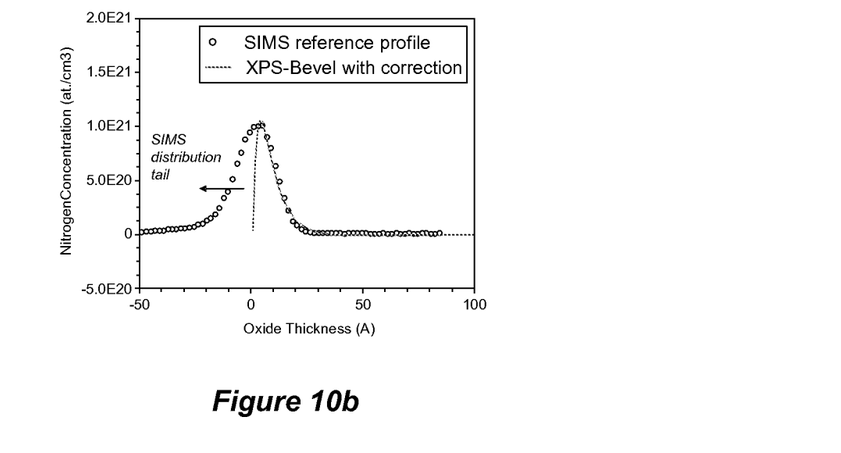
FIG. 10b shows an exemplary XPS-Bevel nitrogen profile incorporating a correction factor in comparison with a SIMS reference profile following an algorithm including a correction factor.

FIG. 10b shows an exemplary XPS-Bevel nitrogen profile incorporating a correction factor in comparison with a SIMS reference profile following a raw algorithm.

The corrected profile using eq. VIIb (and its consequences on the surface quantification of eq. IV, V and VI), is then calibrated as shown in FIG. b. It may be observed that the improvement between the two profiles demonstrates the relevance of the surface correction factor. Also, the best fit is obtained using the same parameters as for FIG. 10a, but introducing a surface correction factor $\alpha_s$=10, which means that the nitrogen dose in the upper slice was overestimated.

The $\alpha_s$ value is strongly dependent on the surface properties of the sample, and of the interaction between the surface and the escaping photoelectrons.

This surface correction factor is advantageous to obtain a good correlation of the XPS-Bevel technique with a SIMS reference profile, and enhances the possibility of leveraging the characteristics of the XPS-Bevel technique in particular in affording a fast and in-line determination of the elemental profile. Furthermore, this technique also provides some meaningful information on the nitrogen binding energy, and it is very well known in the literature that this energy is strongly related to the bonding configuration of the nitrogen in the silicon dioxide matrix (see for example Y. K. Kim, H. S. Lee, H. W. Yeom, D. Y. Ryoo, S. B. Huh, and J. G. Lee, Phys. Rev. B., (2004) 70, 165320.)

The forgoing description provides exemplary embodiments based on nitrogen profile measurement for nitrided SiON on an SI substrate. It will be appreciated that the described technique extends equally to other elements in various films, such as for example high-k/metal gate stacks and SiGe layers and silicon nitride materials.

Figure 11:
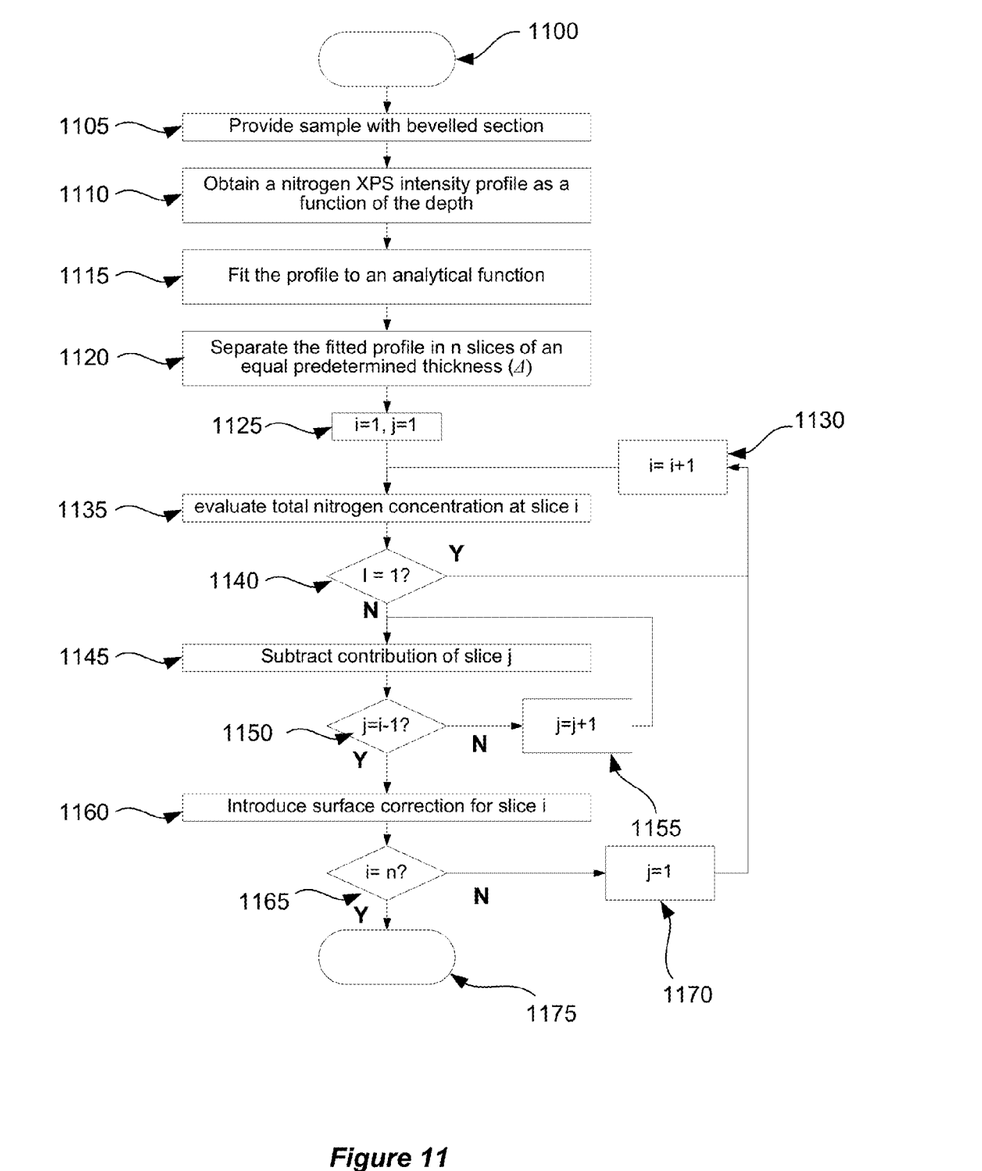
FIG. 11 shows the steps of a method according to the preferred embodiment described with respect to FIG. 10.

FIG. 11 shows the steps of a method according to the preferred embodiment described with respect to FIG. 10.

As shown in FIG. 11, the method starts at step 1100, before proceeding to step 1105 at which the semiconductor wafer sample is provided with a bevelled edge, for example by means of the etching process described above with reference to FIGS. 1 and 2. The method then proceeds to step 1110 at which a nitrogen XPS intensity profile is obtained, for example by measuring XPS intensity at different points along a radius of the sample, as described above with reference to FIGS. 6 and 7. The method next proceeds to step 1115, at which the profile obtained at step 1115 is fitted to a mathematical function, for example in the form of a sum of exponential functions as described above with reference to FIG. 8. The method then proceeds to step 1120 at which the fitted profile is divided into n slices of a given and equal thickness $\Delta$. The method next proceeds to step 1125 at which i and j variables designating a respective slices of said profile are set to 1, thereby designating the slice closest to the substrate. The method then proceeds to step 1145, at which the total nitrogen concentration at slice i is evaluate, for example as described above with respect to FIGS. 9a and 9b. At step 1140 it is determined whether the slice currently under consideration is the first slice (i=1) in which case the method proceeds directly to step 1130 at which I is incremented by one before returning to step 1135. If it is determined at step 1130 that i is greater than one, or in other words that a slice other than the lowest slice 911 is currently under consideration, the method proceeds to step 1145 at which the contribution for the preceding slice j as determined in a previous iteration is retrieved and subtracted from the total nitrogen concentration evaluated for the slice i presently under consideration. The method next proceeds to step 1150 at which it is determined if all of the slices underlying the slice presently under consideration have been taken into account (j=i–1 If it is determined a step 1150 that j is not equal to i–1, in other words that some slices remain to be taken into account, the method proceeds to step 1155 at which j is incremented by one so as to designate the next layer in turn before returning to step 1145. If it is determined a step 1150 that j=i−1 then the method proceeds to step 1160 at which a surface correction factor $\alpha_s$ is applied to the residual nitrogen concentration value for example as described above with reference to FIG. 10b. The method then proceeds to step 1165 at which it is determined whether a final nitrogen concentration value has been determined for all slices (i=n), in which case the method terminates at step 1175. Otherwise the method proceeds to step 1170 at which j is set back to 1 before proceeding to step 1130.

In other words, the result of steps 1125 to 1175 is that the fitted function is evaluated for each slice in turn starting form the lowest, with the final nitrogen concentration for each slice being determined to be the total nitrogen concentration minus the contribution of each preceding slice.

Accordingly there is provided a method of obtaining an elemental concentration profile of a sample said method comprising the steps of obtaining an elemental intensity profile by X-ray Photoelectron Spectroscopy as a function of sample depth, fitting said profile to an analytical function, separating said profile into a plurality of slices of a predetermined equal thickness, and evaluating the fitted function for each said slice in turn starting from that corresponding to the thinnest part of said sample, with the final nitrogen concentration for each slice being determined to be the total nitrogen concentration minus the contribution of every preceding slice.

The preceding embodiments assume that the slices into which the function is divided are of equal thickness. The advantage of using slices of equal thickness is that the concentration can be expressed in a general form (eq. VIIb), which is much more simple to handle for further computing of the data. Nevertheless, in certain circumstances it may be desirable to use slices of differing thickness, for example so as to provide a curve having higher definition for parts of the sample cross section of particular importance in a particular context.

It is a further advantage of the described approach that once XPS measurement has been performed, the wafer can follow a standard cleaning procedure such as:
HF-RCA wet clean
Dry sacrificial oxidation
HF-RCA wet clean Accordingly, the wafer can then be used again for process development.

Although as described above a preferred method of exposing parts of said sample at a range of depths is described based on a circumferential bevelling of the edge of the sample, it is clear that any other convenient.

FIG. 12 shows examples of possible approaches to exposing parts of said sample at a range of depths.

Figure 12A:
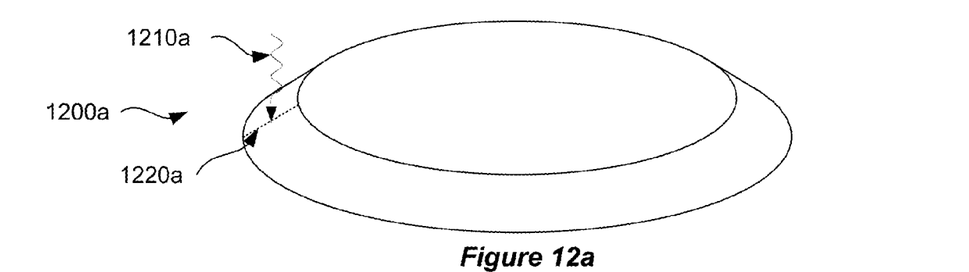
FIGS. 12a, 12b, 12c and 12d show examples of possible approaches to exposing parts of the sample at a range of depths.

FIG. 12a shows the approach used in describing the embodiments of FIGS. 2 to 11. The sample 1200a exhibits circumferential bevelling of the edge thereof which may be achieved in any of the various manners that may occur to the skilled person, in particular as described above. The wavy line 1210a represents the arrival of the XPS waves, which move along the dotted line 1220a so as to access different sample depths.

Figure 12B:
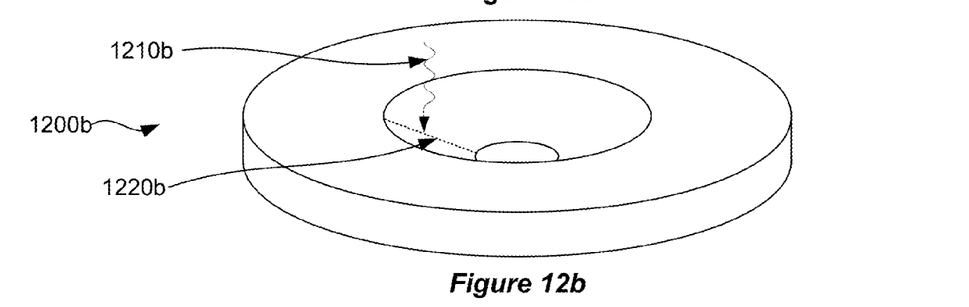

FIG. 12b shows a first alternative approach that may be used in exposing parts of the sample at a range of depths. As shown in FIG. 12b the sample 1200b exhibits an internal coaxial bevelling of an edge around a central aperture in the sample. This aperture and bevel may be achieved in any of the various manners that may occur to the skilled person, in particular as described above. The wavy line 1210b represents the arrival of the XPS waves, which move along the dotted line 1220b so as to access different sample depths.

Figure 12C:
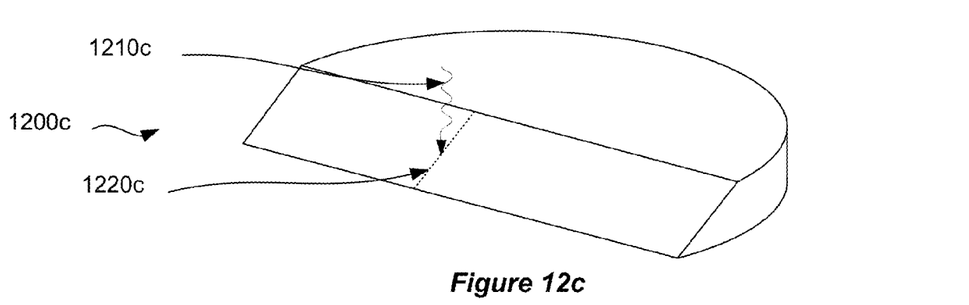

FIG. 12c shows a second alternative approach that may be used in exposing parts of the sample at a range of depths. As shown in FIG. 12c the sample 1200c exhibits a straight bevelled edge describing a chord between two points on the circumference of the sample. This edge and bevel may be achieved in any of the various manners that may occur to the skilled person, in particular as described above. The wavy line 1210c represents the arrival of the XPS waves, which move along the dotted line 1220d so as to access different sample depths.

Figure 12D:
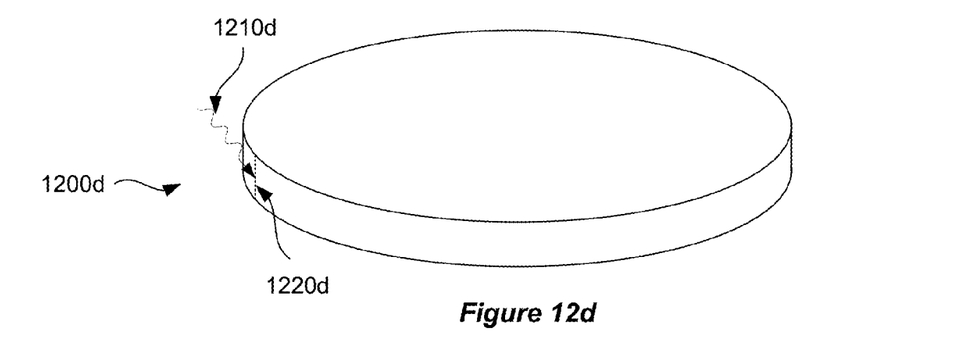

FIG. 12d shows a third alternative approach that may be used in exposing parts of the sample at a range of depths. As shown in FIG. 12c the sample 1200d is unmodified from its conventional cylindrical configuration. The wavy line 1210d represents the arrival of the XPS waves, which move along the dotted line 1220d so as to access different sample depths. As shown, the XPS waves arrive at an angle to the top surface of the sample, and thus also strike the side wall thereof, and therefore permit access to different sample depths.

According to a further embodiment there is provided a method of obtaining an elemental concentration profile of a sample using x-ray photon spectroscopy measurements is described, in which each measurement relates to a different depths in the sample. The sample is shaped so as to provide access to different depths thereof, for example by means of a bevelled edge. Measurements are obtained by at respective positions on a bevelled surface exposing material at each of said depths. The method involves fitting the measurements to a mathematical function, dividing said function into a plurality of equal depth wise slices, determining the elemental (e.g. nitrogen) concentration for the slice corresponding to the thinnest part of said bevel, and then iteratively determining the contribution of each successive slice to the intensity value as being the intensity value measured for that slice minus the intensity value determined to have been contributed by each preceding slice. According to preferred embodiments, a surface correction factor compensating surface effect phenomena is applied to the concentration value calculated for each slice, taking into account factors such as the increased dangling bond density exhibited by surface atoms or variations caused by the atmosphere to which the sample has been exposed.

The invention can take the form of an entirely hardware embodiment, an entirely software embodiment or an embodiment containing both hardware and software elements. In a preferred embodiment, the invention is implemented in software, which includes but is not limited to firmware, resident software, microcode, etc.

Furthermore, the invention can take the form of a computer program product accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

What is claimed is:

1. A method of obtaining an elemental concentration profile of a sample, the method comprising steps of:
   modifying said sample to provide a bevelled section exposing parts of said sample at a range of depth;
   obtaining an elemental intensity profile by X-ray Photo-electron Spectroscopy as a function of said range of depth;
   fitting said profile to an analytical function;
   separating said profile into a plurality of slices of a predetermined equal thickness; and
   evaluating a final elemental concentration value for each said slice of in turn starting from that corresponding to a thinnest part of said sample, where the final elemental concentration value for each said slice is determined to be a total elemental concentration value extracted from said analytical function, minus a contribution of every preceding slice.

2. The method of claim 1, wherein said step of obtaining an elemental intensity profile comprises a step of removing background noise from a measured X-ray Photoelectron Spectroscopy spectrum using a linear subtraction algorithm.

3. The method of claim 1, further comprising a step of applying a surface correction factor to a final nitrogen concentration value determined for each said slice, said surface correction factor compensating surface effect phenomena.

4. The method of claim 3, wherein said surface effect phenomena includes an increased dangling bond density exhibited by surface atoms.

5. The method of claim 3, wherein said surface effect phenomena includes variations caused by atmosphere to which the sample has been exposed.

6. An apparatus comprising means adapted for carrying out steps of:
   preparing a sample to have a bevelled section exposing parts of said sample at a range of depth;
   obtaining an elemental intensity profile by X-ray Photo-electron Spectroscopy as a function of said range of depth;
   fitting said profile to an analytical function;
   separating said profile into a plurality of slices of a predetermined equal thickness; and
   evaluating a final elemental concentration value for each said slice of in turn starting from that corresponding to a thinnest part of said sample, where the final elemental concentration value for each said slice is determined to be a total elemental concentration value extracted from said analytical function, minus a contribution of every preceding slice.

7. A computer readable storage medium having encoded thereon a set of instructions which, upon being executed by a computer, carry out steps of:
   preparing a sample to have a bevelled section exposing parts of said sample at a range of depth;
   obtaining an elemental intensity profile by X-ray Photo-electron Spectroscopy as a function of said range of depth;
   fitting said profile to an analytical function;
   separating said profile into a plurality of slices of a predetermined equal thickness; and
   evaluating a final elemental concentration value for each said slice of in turn starting from that corresponding to a thinnest part of said sample, where the final elemental concentration value for each said slice is determined to be a total elemental concentration value extracted from said analytical function, minus a contribution of every preceding slice.

* * * * *